US008313751B2

(12) United States Patent
Planz et al.

(10) Patent No.: US 8,313,751 B2
(45) Date of Patent: Nov. 20, 2012

(54) COMPOSITIONS AND METHODS FOR THE PROPHYLAXIS OR TREATMENT OF VIRAL DISEASES

(75) Inventors: Oliver Planz, Rottenburg (DE); Stephan Pleschka, Giessen (DE); Hans-Harald Sedlacek, Marburg (DE); Stephan Ludwig, Würzburg (DE)

(73) Assignee: Activaero GmbH, Gemunden (DE)

( * ) Notice: Subject to any disclaimer, the term of this patent is extended or adjusted under 35 U.S.C. 154(b) by 359 days.

(21) Appl. No.: 12/199,694

(22) Filed: Aug. 27, 2008

(65) Prior Publication Data

US 2009/0191207 A1  Jul. 30, 2009

Related U.S. Application Data

(63) Continuation of application No. 10/541,633, filed on Jun. 30, 2006, now abandoned, and a continuation of application No. PCT/DE2004/000012, filed on Jan. 2, 2004.

(30) Foreign Application Priority Data

Jan. 3, 2003  (DE) .................................. 103 00 222

(51) Int. Cl.
*A61K 39/145* (2006.01)
*A61K 39/285* (2006.01)
(52) U.S. Cl. ...................................... 424/209.1; 424/9.1
(58) Field of Classification Search .......................... None
See application file for complete search history.

(56) References Cited

U.S. PATENT DOCUMENTS 5,290,540 A * 3/1994 Prince et al. ................... 424/45
6,107,281 A   8/2000 Furukawa et al.

FOREIGN PATENT DOCUMENTS

DE        3832799 A1   3/1990
WO     WO 02051413 A   7/2002

OTHER PUBLICATIONS

Centers for Disease Control and Prevention, CDC recommends that people with influenza-like illness remain at home until at least 24 hours after they are free of fever (100° F. [37.8° C.]), or signs of a fever without the use of fever-reducing medications., Oct. 23, 2009, Accessed at <<http://www.cdc.gov/h1n1flu/guidance/exclusion.htm>>, Sep. 20, 2010.*
Dewey, Homeopathy in Influenza-A chorus of fifty in harmony, 1921, Journal of the American Institute of Homeopathy, pp. 1038-1043.*
CDC Seasonal Influena (Flu) Basics, 2011, CDC publication, <<online at: http://www.cdc.gov/flu/about/disease/>>, accessed on Nov. 2, 2011.*
Mazur et al., Acetylsalicylic acid (ASA) blocks influenza virus propagation via its NF-kB-inhibiting activity, 2007, Cellular Biology, vol. 9, No. 7, pp. 1683-1694.*
Notification of Reasons for Refusal, JP Application No. 2006-500466, dated Jan. 26, 2010, and English translation thereof, 10 pages.
Primache, et al., In Vitro Activity of Acetylsalicylic Acid on Replication of Varicella-Zoster Virus. Microbiologica, 21, 397-401, 1998.
A. D. Inglot, Comparison of the Antiviral Activity in vitro of some Non-steroidal Anti-inflammatory Drugs. J. gen. Virol. (1969), 4, 203-214.
M. Broggini, et al., Flurbiprofen Versus ASA in Influenza Symptomatology: A Double-Blind Study. Int. Clin. Pharm. Res. VI (6) 485-488 (1986).
R. Bettini, et al., Diclofenac Sodium versus Acetylsalicylic Acid: A Randomized Study in Febrile Patients. J Int Med Res (1986) 14, 95.
P. Bernasconi, et al., Evaluation of a New Pharmaceutical Form of Nimesulide for the Treatment of Influenza. Drugs Exptl. Clin. Res. XI(10) 739-743 (1985).
C. Milvio, MD., Treatment of Influenza Syndrome A Double-Blind Controlled Trial of Nimesulide v. Aspirin. Clinical Trials Journal 1985 vol. 22 No. 1.
S. W. Younkin, et al., Reduction in Fever and Symptoms in Young Adults with Influenza A/Brazil/78 H1N1 Infection After Treatment with Aspirin or Amantadine. Antimicrobial Agents and Chemotherapy, Apr. 1983, p. 577-582, vol. 23, No. 4.
M. H. Grieco, M.D., Therapy of Viral Infections. vol. 58, No. 8, Nov. 1982.
M. Elliott, Zanamivir: from drug design to the clinic. Phil. Trans. R. Soc. Land. B (2001) 356, 1885-1893.
Huang, R T, The New England Journal of Medicine, 1988, vol. 319, No. 12, p. 797.
Broggini, M., et al., Flurbiprofen Versus ASA in Influenza Symptomatology: a Double-Blind Study, International Journal of Clinical Pharmacology Research, VI(6), pp. 485-488, 1986.
Cox, Nancy J., et al., Influenza, The Lancet, vol. 354, pp. 1277-1282, Oct. 9, 1999.
European Search Report, Activaero GmbH, Application Serial No. EP10011214.3-210-7, issued Jan. 3, 2011.
Huang, R. T., et al., Anti-influenza Viral Activity of Aspirin in Cell Culture, The New England Journal of Medicine, vol. 319, No. 12, p. 797 Sep. 22, 1998.
Milvio, C., Treatment of Influenza Syndrome A Double-Blind Controlled Trial of Nimesulide vs. Aspirin, Clinical Trials Journal, vol. 22, No. 1, pp. 111-117, 1985.
Primache, K. et al., In Vitro Activity of Acetylsalicylic Acid on Replication of Varicella-zoster Virus, New Microbiologica, Luigi Ponzio E Faglio, Bologna, Italy, vol. 21, 397-401, 1998.
Younkin, S. W., et al., Reduction in Fever and Symptoms in Young Adults With Influenza A/Brazil/78 H1N1 Infection After Treatment with Aspirin or amantadine, Antimicrobial Agents and Chemotherapy, vol. 23, No. 4, pp. 577-582, Apr. 1983.

* cited by examiner

*Primary Examiner* — Benjamin P Blumel
(74) *Attorney, Agent, or Firm* — Peters Verny, LLP

(57) ABSTRACT

The invention relates to the use preferably of at least one active ingredient for the prophylaxis or therapy of a viral disease, wherein this active ingredient inhibits at least one component of the cellular signal transduction pathway for the activation of the transcription factor NF-kB such that virus multiplication is inhibited. The present invention relates furthermore to the local, preferably aerogenic, administration of the active ingredient according to the invention for inhibiting virus multiplication. The active ingredient according to the invention may be combined with at least one further antivirally effective substance for the prophylaxis or therapy of a viral disease.

5 Claims, No Drawings

COMPOSITIONS AND METHODS FOR THE PROPHYLAXIS OR TREATMENT OF VIRAL DISEASES

STATEMENT OF RELATED APPLICATIONS

This application is a continuation of co-pending U.S. Patent Application Ser. No. 10/541,633, filed Jun. 30, 2006 and entitled "Compositions and Methods For The Prophylaxis Or Treatment of Viral Diseases," which in turn was a National Stage Entry of PCT/DE04/00012filed Jan. 2, 2004 and claimed priority to German patent application Ser. No. 103 00 222.7filed Jan. 2003. U.S. Patent Application Ser. No. 10/541,633, filed Jun. 30, 2006 is hereby incorporated by reference herein in its entirety.

FIELD OF THE INVENTION

The invention relates to a test system for identifying active ingredients, which are suitable for the prophylaxis or treatment of viral diseases, the uses of such active ingredients for preparing a pharmaceutical composition for the prophylaxis or treatment of viral diseases, formulations for such pharmaceutical compositions and methods for preparing such pharmaceutical compositions.

PRIOR ART AND BACKGROUND OF THE INVENTION

Infections by RNA or DNA viruses are a substantial threat to the health of humans and animals. To the RNA viruses belong the negative-strand-RNA viruses, such as for example, influenza viruses or the Borna disease virus. Infections by influenza viruses is the source of large-scale epidemics and cause a large number of fatalities on an annual basis. They are an immense cost factor in the economy, for instance by causing lost work days due to illness. Of substantial economic importance are also infections caused by the Borna disease virus (BDV), in particular those that attack horses and sheep, which have been isolated in man, too, and which have been connected with neurological diseases.

The problem of controlling in particular RNA viruses is the adaptability of the viruses caused by a high fault rate of the viral polymerases. Thus the preparation of suitable vaccines as well as the design of antiviral substances has been very difficult. Furthermore, it has been found that the application of antiviral substances immediately directed against the functions of the virus, has a relatively fair antiviral effect at the early stage of therapy, but will lead very quickly to the generation of resistant variants by mutation. An example is the anti-influenza drug amantadine and its derivatives, which is or are directed against a transmembrane protein of the virus. Within a short time after application, resistant variants of the virus are generated.

Other examples are the new therapeutic agents for influenza reactions that inhibit inhibiting the influenza-viral surface protein, neuraminidase. Hereto belongs, for instance, Relanza. In patients, Relanza-resistant variants have already been found (Gubareva et al., J Infect Dis 178, 1257-1262, 1998). The hopes placed on this therapeutic agent thus could not be fulfilled.

Due to their in most cases very small genomes and therefore limited coding capacity for replication-necessary functions, all viruses have to rely to a large extent on functions of their host cells. By exerting influence on such cellular functions necessary for viral replication, it is possible to negatively affect the virus replication in the infected cell. Then, there is no possibility for the virus to replace the missing cellular function by adaptation, in particular by mutation, in order to avoid the selection pressure. This could already be shown in the example of the influenza A virus with relatively unspecific inhibiting substances against cellular kinases and methyltransferases (Scholtissek and Müller, Arch Virol 119, 111-118, 1991).

It is known that cells have a multitude of signal transduction pathways, by means of which signals acting on the cell are transmitted to the cell nucleus. Thereby the cell is able to react to outside stimuli with cell proliferation, cell activation, differentiation or controlled cell death.

These signal transduction pathways have in common at least one kinase, which activates by phosphorylation at least one protein that transduces the signal.

By observing the cellular processes induced as a result of virus infections, it can be found that a multitude of DNA and RNA viruses activate in the infected host cell preferably by a defined signal transduction pathway, the so-called Raf/MEK/ERK kinase signal transduction pathway. This signal transduction pathway is one of the most important signal transduction pathways in a cell and plays a substantial role in proliferation and differentiation processes (Cohen, Trends in Cell Biol 7, 353-361, 1997; Robinson and Cobb, Curr. Opin. Cell Biol 9, 180-186, 1997; Treismann, Curr. Opin. Cell Biol 8, 205-215, 1996).

The investigation of the role of this signal transduction pathway in cellular decision processes has led to the identification of several pharmacological inhibitors inhibiting the signal transduction pathway, among other places, on the MEK level, i.e. relatively at the beginning of the signal transduction pathway (Alessi et al., J Biol Chem 270, 27489-27494, 1995; Cohen, Trends in Cell Biol 7, 353-361, 1997; Dudley et al., PNAS USA 92, 7686-7689, 1995; Favata et al., J Biol Chem 273, 18623-18632, 1998).

Newer data show that the inhibition of the Ras-Raf-MEK-ERK signal transduction pathway or of another signal transduction pathway, the MEKK/SEK/JNK signal transduction pathway, can drastically inhibit by active ingredients, which relatively selectively inhibit one of the kinases involved in this signal transduction pathway, for instance the MEK or the SEK, the intracellular multiplication of intranuclearly replicating negative-strand viruses, for instance of influenza A viruses and the Borna disease virus (BDV) (Pleschka et al., Nature Cell Biol 3, 301-305, 2001; Planz et al., J Virol 10, 4871-4877, 2001; PCT/DE 01/01292; DE 101 38 912).

Up to now it was known that influenza viruses preferably use the Raf-MEK-ERK signal transduction pathway or the MEKK/SEK signal transduction pathway for their multiplication, and that therefore an inhibition of these signal transduction pathways would lead to a complete inhibition of virus multiplication. Since, however, in a cell the signal transduction pathways have hardly any function closed in itself, but with activation of the one signal transduction pathway, further signal transduction pathways are additionally activated by cross linkages, it can in principle not be excluded that an inhibited signal transduction pathway can be bypassed by the cell as well as by the viruses, and the therapeutic effect of an active ingredient inhibiting a virus multiplication by inhibition of a certain signal transduction pathway could be limited thereby.

Therefore, there is a great need of identifying and using antiviral active ingredients, which act in addition to or as a supplement to those, which inhibit kinases of cellular signal transduction pathways, for instance of the Raf-MEK-ERK signal transduction pathway or of the MEKK/SEK/JNK signal transduction pathway. Such active ingredients have already been described in the documents PCT/DE 01/01292 and DE 101 38 912.

One of the most important signal transduction pathways in the cell is the nuclear factor of kappaB (NF-kB) signal transduction pathway. The central component of this transduction pathway is the heterodimer NF-kB transcription protein complex consisting on the one hand of p50 [formed by proteolysis of NF-kB1 (p105)] or of p52 [formed by proteolysis of NF-kappaB2 (p100)], and on the other hand of p65 (RELA), c-REL or RELB. The most common NF-kB complex is composed of p50 and p65.

The transcription activity of this NF-kB complex is inhibited by the binding of the inhibitor proteins of NFkB (IkB) to the nuclear binding sequence of p65. Thereby, the complex remains in the cytoplasm. An activation of the cell, for instance by growth factors, chemokines, TNF-alpha, Il-1, C40 ligand, LPS or by an infection by viruses will lead to the activation of kinases such as the "NF-kB inducing kinase" (NIK), the kinase TAK, the kinase AKT and possibly also of the kinase MEKK1. These kinases lead to the activation of the "inhibitor of kB (IkB) kinase" (IKK) complex, composed of IKKalpha, IKKbeta and NEMO. Activated IKK phosphorylates IkB and thus leads to its degradation and permits thereby the release, nuclear translocation and activation of the transcription activity of the p50/p65 heterodimer. Another NF-kB complex is composed of p100 and RELB. An activation of the cell by lymphotoxines will lead, probably preferably mediated by NIK, to the activation of IKKalpha. The activated IKK induces the phosphorylation and thus the proteolysis of p100 to p52, which in turn can translocate in the complex with the RELB into the cell nucleus and act there as a transcription factor.

It is known in the art that the activation of the NF-kB signal transduction pathway can be inhibited by i) nonsteroidal antiinflammatory drugs (NSAIDs), such as sulindac (Yamamoto et al., J Biol Chem 274, 27307-27314, 1999; Berman et al., Clin Cancer Res 8, 354-360, 2002) or derivatives of sulindac such as sulindac sulphoxide, sulindac sulphone, sulindac sulphide or benzylamide sulindac analogues (Moon and Lerner, Cancer Research 62, 5711-5719, 2002) or acetylsalicylic acid or salicylic acid (Yin et al., Nature 396, 77-80, 1998) or curcumin (Oncogene 18, 6013-6020, 1999) by inhibition of the IKKbeta, ii) NEMO binding peptides (May et al., Science 289, 1550-1554, 2000), proteosome inhibitors such as PS-341 (Tan and Waldmann, Cancer Res 62, 1083-1086, 2002; Adams Trends Mol Med 8, 49-54, 2002), or iii) antisense nucleotide sequences specific for p65 or p50 (Higgins et al., PNAS-USA 90, 9901-9905, 1993). Up to now these inhibitors were, however, exclusively tested for their use as active ingredients for having influence on inflammation and the growth of tumors, since in both indications the involved cells have an increased activation of the NF-kB signal transduction pathway (Karin et al., Nature Reviews Cancer 2, 301-310, 2002).

To date, it has been postulated that a virus infection, in particular, by an influenza virus, activates the NF-kB signal pathway by the activation of the IKK, and said signal pathway is in turn decisively involved in the expression of antivirally active proteins increased by this infection, for instance interferon (Chu et al., Immunity 11, 721-731, 1999). In agreement with this idea is the finding that the influenza virus-induced activity of the interferon β promoter is strongly reduced in cells, which express a transdominant-negative mutation of IKK2 or IkBalpha (Wang et al., Virol 74, 11566-11573, 2000). On the other hand, there is a hint contradicting these ideas and findings that acetylsalicylic acid, known as an inhibitor of the IKK, is also able to inhibit influenza virus infections in the cell culture, however, such inhibition was observed only beginning from concentrations of 5-10 mM (corresponding to 0.9-1.8 mg/ml). Such concentrations are practically not achievable in blood without substantial side effects from oral administration of acetylsalicylic acid (Huang and Dietsch, New Engl J Med 319, 797, 1988). Acetylsalicylic acid is deemed the most toxic of all readily available analgesics with the smallest therapeutic width (Jones, Am J Ther 9, 245-257, 2002). Huang and Dietsch speculated that an administration by aerosol would result in higher and thus antivirally effective concentrations locally in the respiratory passages. These recommendations have, however, not been realized up to now, since the up to now known clinical side effects alone led, after administration of a dose of 100 mg acetylsalicylic acid otherwise not deemed toxic, to a warning not to take aspirin in case of a virus influenza, particularly by children (user information Z. No. 14.252 of Bayer AG about the acetylsalicylic acid (ASA) preparation Aspirin®).

TECHNICAL OBJECT OF THE INVENTION

It is therefore the technical object of the invention to provide a test system, by means of which improved active ingredients for the prophylaxis or treatment of viral diseases can be found, and to specify pharmaceutical compositions and formulations for such indications.

BASICS OF THE INVENTION AND EMBODIMENTS

The invention is based on the surprising findings that i) active ingredients inhibiting the cellular NF-kB signal transduction pathway are able to inhibit the multiplication of viruses in an organism, ii) smaller concentrations of the active ingredient used according to the invention than derivable from the in vitro data are antivirally effective with local administration, iii) the active ingredient acetylsalicylic acid used according to the invention, administered aerogenically in concentrations of 0.1 to 4 mM, causes a distinct inhibition of the influenza virus multiplication in the lung and in the total organism and a systemic healing effect without impairing the general condition, although such concentrations of the acetylsalicylic acid have not shown in vitro any antiviral effectivity. Higher doses of acetylsalicylic acid, for instance acetylsalicylic acid in concentrations of 10 mM, were comparatively not stronger, and even higher doses (up to 50 mM) were clearly less antivirally effective than the lower concentrations according to the invention. In addition, concentrations over 20 mM turned out to be toxic after aerogenic administration.

The subject matter of the present invention is thus, the use of at least one active ingredient for preparing a pharmaceutical composition for the prophylaxis or therapy of at least one viral disease, the active ingredient(s) acting on at least one component of the NF-kB signal transduction pathway, so that a virus multiplication in the organism is inhibited. Components of the NF-kB signal transduction pathway are for instance: tumor necrosis factor receptor associated factor (TRAF), NF-kB inducing kinase (NIK), mitogen-activated protein kinase kinase kinase 1 (MEKKK1), mitogen-activated protein kinase kinase kinase 3 (MEKKK3), AKR mouse thymoma kinase (AKT), TGFβ activated kinase (TAK1), inhibitor of NF-kB kinase alpha (IKKaplha), inhibitor of NF-kB kinase beta (IKKbeta), NEMO, inhibitor of kB (IkB), RELA (p65), C-REL, RELB, NF-kB1 (p105), NF-kB2 (p100), P50, and P52.

The active ingredients used according to the invention include for instance: inhibitors of a kinase of the NF-kB signal transduction pathway [including nonsteroidal anti-inflammatory substances inhibiting the NF-kB activation, such as phenylalkyl acid derivatives, for instance sulindac (Yamamoto et al., J Biol Chem 274, 27307-27314, 1999; Berman et al., Clin Cancer Res 8, 354-360, 2002) or derivatives of sulindac such as sulindac sulphoxide, sulindac sulphone, sulindac sulphide or benzylamide sulindac analogues (Moon and Lerner, Cancer Research 62, 5711-5719, 2002), salicylic acid derivatives such as salicylic acid itself or acetylsalicylic acid (Yin et al., Nature 396, 77-80, 1998), salkylamide, salacetamide, ethenzamide, diflunisal, olsalazine or salazosulfapyridine, curcumin (Oncogene 18, 6013-6020, 1999), antioxidants such as pyrrolidine dithiocarbamate (PDTC; Piette et al., Biol Chem 378, 1237-1245, 1997), oxicams such as for example piroxicam (Liu et al., J Biol Chem 13, —, 2002), vitamin E and derivatives thereof, such as pentamethyl hydroxychroman (PMC, Hattori et al., Biochem Mol Biol Int 35, 177-183, 1995), 17 beta oestradiol and derivatives thereof (Desphande et al., Am J Reprod Immunol 38, 46-54, 1997), polyphenoles of tea such as, for example (-)-epigallo-catechin-3-gallate (EGCG, Lin et al., Biochem Pharmacol 58, 911-915, 1999), Bay11-1782 Misra and Pizzo Arch Biochem Biophys 386, 227-232, 2001)], peptides inhibiting the interaction of at least two components of the NF-kB signal transduction pathway, including for instance peptides binding to NEMO (May et al., Science 289, 1550-1554, 2000), inhibitors of the proteosome such as PS-341 (Tan and Waldmann, Cancer Res 62, 1083-1086, 2002; Adams Trends Mol Med 8, 49-54, 2002) and lactacystin (Morise and Grisham J Clin Gastroenterol 27, 87-90, 1998), antisense oligonucleotides specifically adding to the DNA sequence or m-RNA sequence coding for a component of the NF-kB signal transduction pathway and inhibiting the transcription or translation thereof, for instance antisense nucleotide sequences specific for p65 or p50 (Higgins et al., PNAS-USA 90, 9901-9905, 1993), dominant-negative mutants of a component of the NF-kB signal transduction pathway; ds-oligonucleotides, which are suitable for the specific degradation of the mRNAs of a component of the NF-kB signal transduction pathway by the RNAi technology according to a method, such as that described by Tuschl et al. (Genes Dev 13:3191-3197, 1999) and by Zamore et al. (Cell 101:25-33, 2000), antibodies or antibody fragments specific for a component of the NF-kB signal transduction pathway, or fusion proteins, containing at least one antibody fragment, for instance a Fv fragment, which inhibit at least one component of the NF-kB signal transduction pathway.

An active ingredient in the meaning of the invention is a substance capable of directly acting on at least one component of the NF-kB signal transduction pathway such that a virus multiplication is substantially inhibited. Further, active ingredients in the meaning of this invention are derivatives of these active ingredients, which are transformed, for instance, by enzymatic fission into an active ingredient according to the invention. Active ingredients in the meaning of the present invention are moreover precursors of active ingredients, which are metabolically transformed into an active ingredient according to the invention.

Preferred is the use of at least one active ingredient according to the invention for the prophylaxis or therapy of viral diseases, which are caused by RNA or DNA viruses, preferably negative-strand RNA viruses, for instance influenza viruses or Borna viruses. For this purpose, the active ingredient according to the invention is administered systemically or locally, for instance dermally, nasally, aerogenically, into a body cavity or a tissue.

Further preferred is the use of acetylsalicylic acid for the prophylaxis or therapy of an influenza viral disease, wherein acetylsalicylic acid is administered nasally or bronchially (aerogenically) in concentrations preferably from 0.1 to 4 mM. The total dose per day for a human should preferably be in the range of 0.1 to 30 mg (nasal) or 0.1 to 70 mg (bronchial). Depending on the application, the lower limit may however also be between 0.1 and 20 mg or 50 mg, respectively. Depending on the application, the upper limit may also be between 1 mg or 2 mg, respectively, and the mentioned maximum values. A daily dose is preferably taken in 1 to 8 administrations, which suitably are distributed over a waking time of 16 hours. A treatment can suitably take place over a period of time of 1 to 7 days or longer. The invention also comprises galenically prepared administration units, and the amount of active ingredient present in an administration unit can easily be calculated according to the treatment plans discussed above.

Another embodiment of the present invention relates to a combination preparation for the prophylaxis or therapy of a viral disease, comprising at least two antivirally acting active ingredients, and at least one antivirally acting active ingredient that inhibits at least one component of the NF-kB signal transduction pathway such that the multiplication of the virus in an organism is inhibited. Preferably, this antivirally acting active ingredient is selected from the active ingredients according to the invention already mentioned above. To the further antivirally acting active ingredients in the combination preparation according to the invention belong either at least one further active ingredient according to the invention and/or at least one antiviral active ingredient, such as: amantadine (1-adamantanamine) and its derivatives, which is or are directed against a transmembrane protein of some influenza A viruses, such as rimantadine, therapeutic agents for influenza infections inhibiting the influenza-viral surface protein neuraminidase. Thereto belong for instance Relanza, inhibitors of the Raf-MEK-ERK signal transduction pathway such as U=126 or other inhibitors, as they were described in the PCT/DE 01/01292, inhibitors of the MEKK/SEK signal transduction pathway or of the components of further signal transduction pathways as they were described in the DE 101 38 912, and synthetic nucleoside analogues such as 3-deazaadenosine and ribavirin.

The combination preparation may be used in the form of a mixture or as individual components for the simultaneous or non-simultaneous application at identical or different places, systemically or locally. The above explanations with regard to dosage forms apply in an analogous manner.

The administration of the combination preparation may take place as a mixture of the active ingredients. The active ingredients may, however, also be administered per administration separately from each other at the same place, for instance systemically by intravenous injection or locally for instance by nasal, aerogenic or dermal administration or by injection into a tissue, or also at different places, simultaneously or non-simultaneously within a certain period of time, when the substance administered first is still effective, for instance, a period of time of three days.

A special type of administration of the active ingredient according to the invention is the aerogenic, i.e. nasal or bronchial administration of the active ingredient for the prophylaxis or therapy of those virus infections, which infect aerogenically. For this purpose, galenic auxiliary means and sprayers of the active ingredient are used, as they are sufficiently known to one of ordinary skill in the art.

Another embodiment of the present invention relates to a test system for identifying active ingredients, which inhibit at least one component of the NF-kB signal transduction pathway such that a virus multiplication is inhibited, comprising a) at least one cell infectible by at least one virus, said cell containing the NF-kB signal transduction pathway and at least one virus infecting the cells, or b) at least one cell infected by at least one virus, wherein at least one component of the NF-kB signal transduction pathway is missing or is defectively mutated.

Cells in the meaning of the present invention are cells from different organs and tissues, for example, cells of the blood or lymph vessels, and cells coating the body cavities. Further are comprised cell cultures, in particular those, which can be acquired from cell banks, such as the American Type Culture Collection ("ATCC"), in particular permissive eukaryotic cell cultures, for example A549, 293, 293T and 293T7 (*homo sapiens*), B82, NIH 3T3, L929 from *mus musculus*, BHK from *cricetus cricetus*, CHO from *cricetulus griseus*, MDCK from *canis familiaris*, Vero, COS-1 and COS-7 from cercopithecus aethiops, and primary embryo fibroblasts from *gallus gallus* (CEF cells).

In the test system according to the invention for identifying active ingredients, it is for instance verified, by the addition of substances, preferably in concentrations of 0.001 μM to 100 μM, and of viruses in a particle number, which are suitable for identifying the selected cell, and determining whether a substance is capable of inhibiting virus multiplication without damaging the cells.

Preferably, the virus used in the test system according to the invention is an RNA or DNA virus, preferably an influenza virus.

In a preferred embodiment, the cell a) of the test system according to the invention comprises at least one overexpressed component of the NF-kB signal transduction pathway, also in the form of constitutively active mutants of these components, in particular by introduction of one gene or several genes coding this component. By this overexpression, substances are detected, which strongly inhibit this component and which can also reach a high intracellular concentration for the inhibition of the overexpressed component. For verification, in a cell b) of the test system according to the invention, the expression of at least one component of the NF-kB signal transduction pathway is inhibited, for instance by the introduction of an antisense DNA or an antisense RNA or by introduction of at least one gene coding for at least one dominant-negative mutant of at least one component of the NF-kB signal transduction pathway.

Another embodiment of the present invention relates to a method for identifying at least one active ingredient according to the invention for the prophylaxis or therapy of viral diseases, said active ingredient(s) inhibiting the multiplication of viruses in the case of viral diseases, comprising the following steps: a) bringing at least one potential active ingredient into contact with at least one test system according to the invention, and b) determining the effect on the multiplication of the viruses.

"Bringing into contact" in the meaning of this invention may for instance take place by the addition of the active ingredients into a nutrient medium of a cell culture or by local or systemic administration of the active ingredients to an organism.

"Bringing into contact" in the meaning of this invention further comprises the conventional methods of the prior art that permit the introduction of substances into intact cells, for instance, by infection, transduction, transfection and/or transformation and further methods known to one of ordinary skill in the art. These methods are in particular preferred, if the substances are viruses, naked nucleic acids, for instance antisense DNA and/or antisense RNA, viroids, virosomes and/or liposomes, and virosomes and liposomes are also suitable for introducing further active ingredients into the cell, in lieu of a nucleic acid molecule.

The determination of the effects on virus multiplication takes place for instance by plaque assays or by determination of the HA units for comparing the virus titer of treated and not treated infected cells.

Another preferred embodiment of the present invention relates to a method for preparing a drug for the prophylaxis or therapy of at least one viral disease, said drug inhibiting the multiplication of viruses in the case of viral diseases, comprising the following steps: a) executing a test system according to the invention, and b) reacting the identified active ingredient(s) dosed in a physiologically effective dosage with at least one auxiliary and/or additional substance and a defined galenic preparation.

Preferably, the active ingredient according to the present invention is prepared for local or systemic administration into an organism by means of the methods and auxiliary and/or additional substances known to one of ordinary skill in the art for a drug.

Suitable auxiliary and additional substances, for example, those substances for the stabilization or preservation of the drug or diagnostic agent are well known to one of ordinary skill in the art (see e.g. Sucker H. et al., (1991) Pharmazeutische Technologie, 2nd edition, Georg Thieme Verlag, Stuttgart). Examples of such auxiliary and/or additional substances are physiological common salt solutions, Ringer's dextrose, dextrose, Ringer's lactate, demineralized water, stabilisators, antioxidants, complex-forming agents, antimicrobial compounds, proteinase inhibitors and/or inert gases.

The local administration may, for instance, nasally or aerogenically be made on the skin, on the mucous membrane, into a body cavity, into an organ, into a joint or into the connective tissue. The systemic administration takes place preferably into the blood, into the peritoneal cavity or into the abdominal cavity.

The drug preparation comprising the active ingredient according to the invention depends on the type of active ingredient and the way of administration and may, for instance, be a solution, a suspension, an ointment, a powder, a spray, or another inhalation preparation. Preferably, nucleotide sequences are inserted by methods well known to one of ordinary skill in the art into a viral vector or a plasmid and reacted with auxiliary substances for cell transfection. To these auxiliary substances belong, for example, cationic polymers or cationic lipids. Antisense oligonucleotides are derivatized by methods familiar to one of ordinary skill in the art, in order to protect them from enzymatic degradation by DNAses or RNAses.

The active ingredient according to the invention may be present in the form of a salt, ester, amide or as a precursor, and preferably only such modifications of the active ingredient are used that do not cause any severe toxicity, irritations or allergic reactions in the patient.

The active ingredient is mixed under sterile conditions with a physiologically acceptable carrier substance and potential preservation agents, buffers or driving agents, depending on the application. Such carrier substances for the drug preparations are familiar to one of ordinary skill in the art.

Preferably, the active ingredient according to the invention is administered in a one-time dose, in particular preferably in several doses, and the individual doses do not exceed the maximum tolerable dose (MTD) of the respective active ingredient for humans. Preferably, a dose is selected that is half the MTD. The daily dose may be administered once a day or in several portions over the day, preferably in approximately identical intervals.

According to the present invention, the administration may take place either locally or systemically, only on one day or daily over several days or at every second or third day over several weeks, until a therapeutic effect is visible.

Example 1

Test System for Identifying Antiviral Active Ingredients

Cell lines were prepared by means of retroviral transduction of the human lung epithelial cells, A549, the canine kidney epithelial cells, MDCK, and the monkey cells, Vero, cell lines were prepared, which stably express either a dominant-negative form of the IKK (IKK KD) or a dominant-interfering mutated form of the inhibitor of NF-kB, mIkb. Furthermore, corresponding lines were also generated, which express an active form of the IKK (IKK EE). The constructs as well as their efficiency with regard to the NF-kB mediated gene expression in cells have already been described (Denk et al., J Biol Chem 276, 28451-28458, 2001).

For generating the stable cell lines, the respective cDNAs for IKK KD, mIkB and IKK EE were cloned in sense orientation into the retroviral expression vector pCFG5 IEGZ (Kuss et al., Eur J Immunol 29, 3077-3088, 1999). Beside the messenger RNA of the 'gene of interest', the vector DNA also codes for the messenger RNA of the "green fluorescent protein" (GFP), which during the protein synthesis is expressed by an internal ribosome binding site. This permits the identification of stably transduced cells by flow cytometry. Furthermore, the vector mediates a resistance against the antibiotic Zeocin. The various expression constructs and the empty vector were transfected (Denk et al., J Biol Chem 276, 28451-28458, 2001) by means of the calcium phosphate precipitation method into the virus-producing cell line øNX (Grignani et al., Cancer Res 58, 14-19, 1998). The transfection efficiency was checked after 24 hours by means of the GFP expression and was in the order of 70-80%. The cells were then selected for approx. 2 weeks with 1 mg/ml Zeocin in the medium.

For the infection of the various target cells (A549, MDCK, Vero) with the recombinant viruses, the retrovirus-containing medium supernatants of the virus-producing cell lines were filtrated, reacted with 5 µg/ml Polybrene (Sigma) and applied to fresh cells. The infection took place during two centrifugations (1,000 g) of 3 hours each on two successive days. Stably transduced cells were selected 24 hours after infection for another two weeks with 400-600 µg/ml Zeocin in the medium supernatant. After the generation of the stable cell lines, these as well as wild-type influenza A viruses were infected as described below, and the virus titers of cells, which stably carried the vector, IKK KD, mIkB and IKK EE, were determined in comparison to the titer from the supernatant of wild-type cells.

In parallel, MDCK cells were transiently transfected with the same constructs by means of the transfection reagent Lipofectamine (Life Technologies) according to standard methods (Ludwig et al., J Biol Chem 276, 10990-10998, 2001). The transfection efficiencies were >60%. 24 hours after the transfection, the infection by the influenza A virus strain fowl plague virus (FPV) with a multiplicity of the infection of 1 (M.O.I.=1) was performed. Another 24 hours after the infection, the titers of the newly formed viruses in the cell culture supernatant were examined in standard plaque assays for MDCK cells. Here, too, the virus titer of influenza A virus-infected cells, which were transfected either with the empty vector or constructs expressing IKK KD, mIkB and IKK EE, were compared.

The following results were obtained. A comparison of the virus titers of influenza A virus-infected MDCK cells, which before had been transfected either with the empty vector or a construct expressing IKK KD or mIkB, showed that in cells expressing IKK KD or mIkB, the multiplication of the viruses was inhibited after 24 hours by 50-70%. Correspondingly, in the cells expressing the active form of IKK, IKK EE, an increase of in the virus multiplication was found. These results were reproducible in several independent batches. Corresponding results could also be obtained in the stable A549, MDCK and Vero cell lines expressing IKK KD, mIkB or IKK EE, and the biggest effects were observed in stably transfected A549 cells. Here an inhibition of the NF-kB activation by IKK KD or mIkB led to an up to 10-fold reduction in the virus titers, whereas a constitutive activation of the signal pathway by stable expression of IKK EE increased the virus yield by a factor of 10. These findings show that the activation of IKK and NF-kB is essential for the influenza virus multiplication, and that the specific inhibition of the IKK/NF-kB signal modules leads to a significant reduction in virus production.

Example 2

Inhibition of the NF-kB Viral Activation and Reduction of the Influenza Viruses in Vitro 2.1: Acetylsalicylic Acid (ASA).

Salicylates, such as ASA or sulfasalazines are widely used clinically as pain alleviating and anti-inflammatory agents. Newer publications show that these substances are direct and effective inhibitors of the IKK (Yin et al., Nature 396, 77-80, 1998; Weber et al., Gastroenterology 119, 1209-1218, 2000) and can inhibit in vitro the multiplication of influenza viruses (Huang and Dietsch, New Engl J Med 319, 797, 1988). Thus, as a positive control, ASA was used. Lung epithelial cells A549 were treated with increasing concentrations of ASA in the range from 0.01 mM-5 mM. These concentrations remained in the culture medium during the full experiment. One hour after treatment, the infection by the influenza A virus strain fowl plague virus (FPV) with a multiplicity of the infection of 1 (M.O.I.=1) was performed. Another 24 hours after the infection, the titers of the newly formed viruses in the cell culture supernatant were examined in standard plaque assays for MDCK cells.

In a second batch, MDCK cells were treated one hour before the infection or two and four hours after the infection with 5 mM ASA. Infection and detection of the newly formed viruses was made as described above.

The following results were obtained. After comparison of the virus titers of A549 culture supernatants of non-ASA treated to ASA treated cells after 24 hours, a concentration-dependent inhibition of the virus multiplication was found, which however was only distinct with 5 mM and comprised 2 log steps. A corresponding inhibiting effect (>2 log steps) of 5 mM ASA could also be observed for infected MDCK cells, and here an addition of ASA 4 h after the infection still caused a reduction of the virus titers by a factor of 10.

2.2 Pyrrolidine Dithiocarbamate (PDTC).

Antioxidants such as pyrrolidine dithiocarbamate (PDTC) are well known as inhibitors of NF-kB activation (a survey can be found in: Piette et al., Biol Chem 378, 1237-1245, 1997). Therefore, it was examined whether this substance class also inhibits the influenza virus multiplication. A549 cells were treated one hour before infection with PDTC in concentrations of 3-24 micromolars. Infection and detection of the newly formed viruses 24 h pi was made as described for ASA in the presence or absence of PDTC during the full experiment.

The following results were obtained. PDTC treatment, too, led to a concentration-dependent inhibition of the virus titers in A549 cells up to an approx. 10-fold reduction with administration of the maximum employed concentration of 24 micromolars. These data show that the IKK and NF-kB inhibiting agents ASA and PDTC, analogous to the effect of dominant-negative mutants from the NF-kB signal module, have a significant inhibiting effect on influenza virus multiplication in cell culture.

Example 3

Effect of ASA on Influenza Infection in Mice 3.1 IP/Parenteral Administration.

C57 Bl/6 mice were nasally infected by 5,000 pfu/20 µl influenza virus (fowl plague virus, FPV). 30 min before the infection, 500 µl ASA (50 mM=9 mg/ml PBS, Sigma-Aldrich Steinheim) were i.p. injected, then ASA (50 mM=9 mg/ml) was administered continuously in drinking water. For control purposes, PBS was injected or administered. Body weight, death rate and survival time were determined. 30 mice per group were treated.

The following results were obtained. Whereas in the control group, all animals died of influenza, in the ASA group approx. 20% of the animals survived the infection. Further, the average survival time of the dead animals was clearly longer than in the control group. ASA in concentrations of 50 mM, however, led to a distinct reduction in body weight because of the toxic dose.

3.2 Aerogenic Administration.

C57 Bl/6 mice were nasally infected by 5,000 pfu/20 µl and 10,000 pfu/20 ml, respectively, influenza virus (fowl plague virus, FPV). At day 0 of treatment, 30 min after the infection, a tracheotube was introduced into the mice after using an anesthetic (IP injection of 300 µl Ketamin/Rompun; Serum Werk Bemburg; Bayer A G Leverkusen), and by means of a nebulizer (Hugo Sachs Elektronik-Harvard App. GmbH March-Hugstetten), aerosol (administration of 600 µl) comprising 2 mM (=0.36 mg/ml PBS), 10 mM, 20 mM or 50 mM ASA (sigma-Aldrich Steinheim) or for control purposes, PBS alone was administered. This aerogenic administration of the substances to be tested was repeated in some groups on days 1, 2, 3 or 1, 2, 5 and 6. In other groups, the treatment with ASA was performed on days 3, 4, 5, 6 after the infection. 5-6 animals per group were treated. Body weight, death rate and survival time were determined. In another experiment, after treatment with ASA on day 1, the animals were killed on day 3, and the virus concentration in the lung tissue was determined.

The following results were obtained. Smaller doses of ASA more clearly reduced the viruses in the lung than higher doses. ASA was toxic beginning from 20 mM (reduction of the body weight). Whereas in the control group all animals died of influenza, in the groups treated with low non-toxic doses (2 mM) of ASA, approx. 40% survived the infection. Further, the average survival time of the dead animals after ASA treatment was clearly longer than for the control group.

The results of the in vivo experiments according to examples 3.1 and 3.2 show that the single or multiple (up to 3) daily aerogenic administration of ASA in low non-toxic doses, i.e. doses from 0.1 mg/kg to 300 mg/kg body weight, in particular 10 mg/kg to 100 mg/kg, preferably 20 mg/kg to 50 mg/kg, for instance 30 mg/kg, will lead to a distinct therapeutic effect against a fatal disease induced by nasal administration of the influenza virus. The formulation should be selected such that the pharmaceutical composition to be aerogenically administered comprises ASA in concentrations below 2 mM, preferably 0.01 mM to 1.99 mM, most preferably 0.1 mM or 0.5 mM to 1.5 mM, for example 1 mM. The liquid phase amount of aerosol has to be calculated and set up according to the above daily doses under consideration of the employed concentration in the liquid phase. The latter may, for example, be obtained with conventional spraying devices, which spray defined amounts of a solution as an aerosol.

The invention claimed is:

1. A method for the therapy of an influenza viral disease caused by RNA virus, wherein said RNA virus is an influenza virus, said method comprising a step of administering to a subject infected with influenza virus, acetylsalicylic acid formulated in a galenic preparation comprising said acetylsalicylic acid in a concentration limited to from 0.1 to 4 mM, wherein when said preparation is administered nasally, bronchially, or aerogenically it results in inhibition of the influenza virus multiplication.

2. The method of claim 1, wherein said preparation is administered aerogenically or bronchially in a total amount of said acetylsalicylic acid per one administration unit in a range of from 0.1 to 70 mg.

3. The method of claim 2, wherein said preparation is administered from 1 to 8 times a day for 1 to 7 days, provided that the total amount of said acetylsalicylic acid does not exceed 70 mg per day.

4. The method of claim 1, wherein said preparation is administered nasally in a total amount of said acetylsalicylic acid per one administration unit in a range of from 0.1 to 30 mg.

5. The method of claim 4, wherein said preparation is administered from 1 to 8 times a day for 1 to 7 days, provided that the total amount of said acetylsalicylic acid does not exceed 30 mg per day.

* * * * *